US008162662B2

(12) United States Patent
Cofrë Gaete

(10) Patent No.: US 8,162,662 B2
(45) Date of Patent: Apr. 24, 2012

(54) BUCCAL DEVICE FOR ISOLATING THE OPERATING FIELD

(76) Inventor: Maria José Cofrë Gaete, San Pedro de la Paz (CL)

( * ) Notice: Subject to any disclaimer, the term of this patent is extended or adjusted under 35 U.S.C. 154(b) by 306 days.

(21) Appl. No.: 12/474,228

(22) Filed: May 28, 2009

(65) Prior Publication Data

US 2010/0233652 A1 Sep. 16, 2010

(30) Foreign Application Priority Data

Mar. 12, 2009 (CL) .................................... 584-2009

(51) Int. Cl.
*A61C 5/12* (2006.01)
*A61C 5/14* (2006.01)
(52) U.S. Cl. ........................................................ 433/138
(58) Field of Classification Search .......... 433/136–140, 433/91–94, 215, 229; 600/237–240, 242, 600/243; 606/232, 228, 144; 128/859–861, 128/848; 601/38
See application file for complete search history.

(56) References Cited

U.S. PATENT DOCUMENTS

| | | | | |
|---|---|---|---|---|
| 1,306,697 | A | * | 6/1919 | Ivory ............................ 433/139 |
| 3,406,452 | A | | 10/1968 | McConville |
| 3,781,994 | A | | 1/1974 | Hesselgren |
| 4,204,329 | A | | 5/1980 | Kahn |
| 4,261,697 | A | | 4/1981 | Newitter |
| 4,583,946 | A | | 4/1986 | Shanel |
| 4,600,387 | A | | 7/1986 | Ross |
| 4,820,155 | A | | 4/1989 | Sauveur |
| 5,890,899 | A | | 4/1999 | Sclafani |
| 6,299,446 | B1 | | 10/2001 | Ahlers |
| 6,648,642 | B1 | | 11/2003 | Horvath et al. |
| 2004/0126739 | A1 | | 7/2004 | Heasley |
| 2004/0170945 | A1 | | 9/2004 | Heasley |
| 2004/0209224 | A1 | * | 10/2004 | Heasley ......................... 433/139 |
| 2007/0172793 | A1 | * | 7/2007 | Doenges et al. ............... 433/139 |

FOREIGN PATENT DOCUMENTS

| | | |
|---|---|---|
| ES | 2 092 924 | 12/1996 |
| WO | WO 89/09032 | 10/1989 |
| WO | WO 96/29952 | 10/1996 |
| WO | WO 02/080802 A2 | 10/2002 |
| WO | WO 02/096313 A1 | 12/2002 |
| WO | WO 2005/055853 A2 | 6/2005 |
| WO | WO 2007/115144 A2 | 10/2007 |
| WO | WO 2008/040107 A2 | 4/2008 |

\* cited by examiner

*Primary Examiner* — Todd Manahan
*Assistant Examiner* — Yogesh Patel
(74) *Attorney, Agent, or Firm* — Foley & Lardner LLP; Antoinette F. Konski; Alex Y. Nie

(57) ABSTRACT

The invention relates to dental devices for isolating a working area, comprising a substantially concave main piece having two upper ends and a substantially round edge on a lower area of the main piece, the round edge being adaptable to a patient's mouth; a substantially concave lower cover attached to the lower area of the main piece; two removable pieces each attached to each of the two upper ends of the main piece; and two upper covers each attached to each of the two removable pieces, the upper covers each having a protuberance to allow attachment of a rubber dam. Also provided are methods for providing isolation of a working area in a patient's mouth.

9 Claims, 11 Drawing Sheets

BUCCAL DEVICE FOR ISOLATING THE OPERATING FIELD

CROSS-REFERENCE TO RELATED APPLICATIONS

This invention claims priority under 35 U.S.C. §119(a) to Chilean Application No. CL 584-2009, filed on Mar. 12, 2009, the contents of which are incorporated by reference in their entirety into the present disclosure.

In dentistry, devices for establishing absolute isolation inside the mouth are essential, especially when working with composite resin amalgam, since they allow it to keep its physical and chemical properties, as well as facilitate its adhesion to the tooth. In the case of minor restoration work, particularly in the upper arch, this is enough to avoid contamination.

In general, mouth isolation permits the control of oral fluids, keeps the operating area dry and free from contamination, retracts gum tissue, cheeks, lips and tongue, and prevents possible injuries from instruments. It also prevents accidental contact with instruments, and the lodging of metallic fragments, composite resins and bits of dental tissue in the surrounding mouth tissue and in the pharynx, reducing work time, facilitating the operator's task, and providing a guarantee of greater safety and higher quality treatment.

Isolation procedures using rubber dams, dam frames, clamps, punchers and clamp holders are well-known. Although the rubber dam can generally be placed in position rapidly, in some cases there are difficulties with normal placement, for example in patients with a fixed partial prosthesis, orthodontic appliances, little permanent dental structure, or when treatment of several adjacent teeth needs to be carried out. The literature has reported a series of complications that have occurred in dental practice because of allergic reactions to the natural latex used for dams, as well as the use of clamps that can cause injury to dental and periodontal tissue.

INDUSTRIAL PROPERTY STATE

A search was carried out in the main patent offices in Chile and the rest of the world and some documents of relevance to the present invention were found, as follows:

1. —U.S. Pat. No. 3,406,452 (1968): Dental rubber dam frame.

This technology protects a frame that is retractable in relation to the patient's face and that is preferably in the form of a U. The lower part of this device is curved, in order to support the chin area and has no sharp angles. This invention has a member that is rounded at the upper ends of the frame.

2. —U.S. Pat. No. 3,781,994 (1974): Arrangement for separating an area of operation or treatment in the oral cavity.

This invention protects a device for separating a small or large section of the oral cavity for the purpose of dental treatment. It consists of an elastic sheet with at least one hole to place over a tooth or group of teeth, with a hollow built-in frame. This system is inflatable as it acts as a pocket that allows the evacuation of waste matter from the inside of the mouth.

3. —U.S. Pat. No. 4,204,329 (1980): Rubber dam holder for use during endodontic therapy.

This invention protects a frame or holder supporting a sheet of elastomeric material external to the oral cavity of the patient during endodontic therapy. This frame consists of two L-shaped structures that when attached in the middle produce a U, the base of which forms a convex configuration, so that each element of the frame is parallel to the patient's cheek. In addition, this invention includes a rubber dam that isolates the teeth in the rest of the oral cavity. This dam is placed from outside the frame by means of barbs that are an integral part of the frame.

4. —U.S. Pat. No. 4,261,697 (1981): Evacuating rubber dam frame.

This invention protects a frame with an evacuating rubber dam. The frame has a hollow part that collects any fluid from the rubber dam. The structure has a U shape that is retractable in relation to the patient's face. The hollow part that collects the fluid is the horizontal arm that connects the base of the members forming the frame.

5. —U.S. Pat. No. 4,600,387 (1986): Rubber dam frame for dental work.

This invention patent protects a device consisting of an elliptical plastic frame with two-members, between which is stretched a rubber dam sheet, leaving an opening for the upper or lower teeth. To assemble the dam, the frame is bent along its minor axis to place it in the patient's mouth. The dam may be cut or punched to isolate one or more teeth from the rest of the mouth.

6. —U.S. Pat. No. 4,583,946 (1986): Holder for rubber dental dam.

This invention patent protects a facial frame made of rigid plastic, which is water and heat resistant and self-attaching. The frame is U shaped, with a curved bar at its base supported by pivots next to the chin and surrounds most of the patient's face. The frame includes fasteners for securing a dental dam, preferably made of a thin rubber sheet. Other fasteners are positioned so that dental tape may be used to tie the frame to the patient's head. This frame was presented in two sizes, one for adults and one for children.

7. —U.S. Pat. No. 4,820,155, presented to the United States Patent and Trademark Office (1989): Dam frame for use during endodontic surgery.

This patent protects a frame consisting of at least two members connected by two hinges that only open in one direction, forming a closed loop. This frame supports a rubber membrane. The frame members can be folded to give easy access to the mouth cavity, maintaining aseptic conditions around the tooth or teeth isolated by the dam.

8. —Application for a world invention patent WO1989/009032 (1989): Unitary preassembled disposable intraoral rubber dam device.

This technology protects a disposable device that comprises a resilient flexible plastic frame, in addition to an elastic latex membrane. The frame has a predetermined configuration and a memory characteristic such that when pressure applied to distort the frame member is relaxed, the frame member returns substantially to its predetermined configuration. The perimeter of the membrane is secured to the frame in the same plane, maintaining its tension. The frame is made of low-density polyethylene.

f9. —Invention patent from the Spanish Patent Office ES2092924 (1996): Dispositivo para el aislamiento del campo operatorio en boca con dique de goma en apoyo mucoso. (Device to isolate the working area in the mouth by means of a rubber dam on mucous support)

The following technology protects a device to isolate the working area in the mouth with a rubber dam. This device consists of three pieces, two of which are curved in the form of a U, joined by hinges permitting variable opening angles. The third piece is elongated and longitudinally curved with end ears, one of which has a slot and the other a widened head axis, incorporating the U-shaped pieces in the base section. These elements have an elastic lineal covering so that they can rest directly on the gums. The pieces include pivots to secure the rubber dam and an elastic covering that prevents damage to the mucous support.

10. —Invention patent at the world patent office WO9629952 (1996): Intraoral vacuum retractor foldable in half comprising two U-shaped members.

This invention protects a metal device with a plastic covering, designed to be placed completely inside the oral cavity. It includes a frame, an external portion with two members in the form of a U, joined at the end arms, with enough elasticity to allow it to be placed manually in the mouth. The device is equipped with one or more segments reinforcing the external part of the frame, as well as accessories for suctioning the fluids out of the oral cavity.

11. —U.S. Pat. No. 5,890,899 (1999): Dental isolator.

This invention protects a dental device that includes a buccal member and a lingual member, placed on each side of the patient's mouth to isolate the buccal and lingual sides of the patient's mandibular teeth, respectively. In addition it has an extension to secure it to the chin. The upper part includes a U-shaped section that attaches to the maxillary teeth. The buccal member can be adapted to the patient's cheek at a distance from the mandibular teeth. The device has a section for collecting oral fluids, including a suction tube.

12. —U.S. Pat. No. 6,299,446 (2001): Rubber dam holder.

This invention patent protects a holder for a rubber sheet dam that comprises a frame including a cross-member, a leg connected at one end, leaving the other free. In addition, it has a secondary unit that is substantially congruent to the first frame member. It has hinges with pins connected to the free ends of the legs, where the holder can be opened and closed.

13. —Invention patent application at the world patent office WO2002096313 (2002): Rubber dam.

This patent application protects a rubber dam for isolating one or more teeth in the mouth of a patient. Said dam comprises an annular perioral frame to be placed outside the mouth, an elastic film-type cover to be inserted with the frame, which includes a form of bag for insertion into the oral cavity, as well as fasteners for attaching the cover in the mouth. This device remains in a state of tension in the oral cavity because it is attached at different points in the patient's mouth.

14. —Patent application at the world patent office WO2002080802 (2002): General field isolation rubber dam.

This technology protects a general field isolation rubber dam with particular applicability in the field of dentistry. The device comprises a sheet of elastomeric material and an operative insert in the rubber sheet, which may be elastic, malleable, resilient, deformable or rigid. This system is usually in the form of a closed loop with openings for defining an operative field created in the rubber dam material inside the closed loop. The use of this device as a method for isolating a field in a clinical procedure is also protected.

15. —U.S. Pat. No. 6,648,642 (2003): Rubber dam.

This invention protects a rubber dam in the form of a bag or that can be adapted to a bag shape and can be placed in the oral cavity. On its forward end it is rolled up and stretched onto a rubber-dam frame. The technology includes a flexible cover, a frame that can be placed outside the patient's mouth around the teeth, where the cover is loose, a form of bag that is closed on the side and on the first end, where an external margin of this cover is joined to the opposite end and connected to the frame. The dam cover can be cut or opened in the operating field. A rubber or adhesive can be used to isolate the tooth and protect the operating field. This device requires fasteners that do not traumatize the tooth. It is easy to install to isolate the tooth and gums. The main structure of this device can be made of flexible plastic or some other elastic material arranged around an opening in the cover, which comprises two concentric arcs. In addition, the invention includes fasteners for placing the rubber dam in the desired position and an adhesive area for placing the rubber cover between the arcs.

16. —US invention patent application 2004126739 (2004): Rubber dam frame with improved retraction, stability and safety characteristics.

This technology claims a frame with a rubber dam, provided with two vertical members that are connected by a single horizontal lower member and two horizontal upper members. The frame has a central curved part in the upper area of the nasal concavity for the patient's comfort when the rubber dam material is placed and this same mechanism stops the material obstructing the nose and impeding the patient's breathing. The frame has a circumferential design to eliminate dangerous protuberances and provide a better means of fastening the rubber dam, due to an increase in the distribution of the tensile forces of the dam membrane. This system gives the membrane greater stability, in addition to ensuring the comfort and safety of the patient. The frame can be made of steel or a similar metal, or the group consisting of rigid or malleable, resilient plastic materials. The membrane for this dam can be inserted in the arc at the moment of manufacture or be attached later to the outside of the frame. The invention also protects a method of preventing the obstruction of the nose and mouth of the patient when the rubber dam is in use.

17. —US invention patent 2004170945 (2004): General field isolation rubber dams without operative inserts which isolate the dental alveolar arch for dental treatment.

This invention protects a rubber dam for isolating an operating field, with particular application to dentistry, in addition to a method for isolating tissues. The device consists preferably of a semi-translucent elastic membrane with a central cleft opening in the dam, through which a group of teeth and their soft tissues protrude for treatment. It can be made from rigid or malleable, resilient elastic materials. It is provided with an adhesive that is applied to the dam surface, for attaching the rubber dam to the dental alveolar tissue. This adhesive can be made from water-insoluble groups and groups with limited water solubility, in addition to pressure-sensitive adhesives, activated chemically and photo-activated. The method includes inserting the rubber dam in the isolation field around a central opening inside the oral cavity, covering a segment of the dental alveolar arch and allowing a group of teeth and associated gingival tissues to protrude through a split or central opening in the dam, then adjusting the clamp on the dam to keep it in the mouth, then applying a barrier on the mesh around the outside of the operating site, and finally applying a polymer to attach the mesh and the dam.

18. —Patent application at the world patent office WO2005055853 (2005): Rubber dams with operative inserts and integrally attached external frames which resist the external vector forces of displacement and effectively isolate dental anatomical structures of the alveolar arch.

This invention patent application protects a device that forms a rubber dam, in addition to a method of assembling this device with an operative insert. The device comprises a sheet of elastomeric material, an insert in which the sheet is placed and an integrally attached exterior frame. This insert as well as the integrally attached frame is molded from elastomeric material and they are both adhered to the external surface of the material. The operative insert and the integrally attached frame can be or not be integrally attached to each other.

19. —Patent application at the world patent office WO2007115144 (2007): Methods, devices, systems and kits for isolating teeth.

This technology protects a method, a device, a system and a kit for isolating teeth. The device comprises an element with a predetermined form that can be inserted in the oral cavity, in addition to another element that does not have a pre-established form. This device is adapted and configured to isolate the working field of gingival tissues and of fluids. It consists of a flexible interior structure adapted and configured for operating inside the alveolar arch; a flexible exterior structure connected to the interior structure, adapted and configured for operating on the external surface of the alveolar arch; in addition to a structure of the same particularities, but located on the lower jaw. It has a tongue deflector and an inflatable membrane adapted and configured for isolating one or more dental and gum regions. This system contains a lumen for extracting fluids from the cavity interior, in addition to a dispenser adapted and configured for administrating a topical anesthetic. The method includes the steps for inserting the dental device adapted and configured for collecting fluids from an alveolar and gingival process, then attaching the fluid collection appliance to the oral cavity device, and finally isolating the working field from the fluids during the procedure.

20. —Patent application at the world patent office WO2008040107 (2008): Dentistry isolator.

This technology protects a rubber dam with a special design that simulates both the right side and the left side of the oral cavity, so that it can be used in both sides of the patient's mouth, including the upper or lower dental arches. The edges of this device are always outside the mouth; its form can be elliptical, square or rectangular, small or large, permitting the use of a thin rubber sheet as an alternative to a conventional frame. The invention consists of a structure made of rubber that is thicker than in conventional rubber dams.

DESCRIPTION OF THE INVENTION

This invention is a buccal device for isolating the operating field. This device has a U-shaped form, concave towards the center and with rounded edges. It is adaptable to the mouth of the patient, because the volume of its pieces is directly related to the folds that form in the face and support areas such as the chin and below the nostrils. This technology comprises six parts that can be assembled together (see FIGS. 1 and 2A to 2C):

a fixed lower piece or main piece (A);
a lower cover (B);
two removable pieces (one left and one right) (C); and
two upper circular covers (D).

Figure 1:
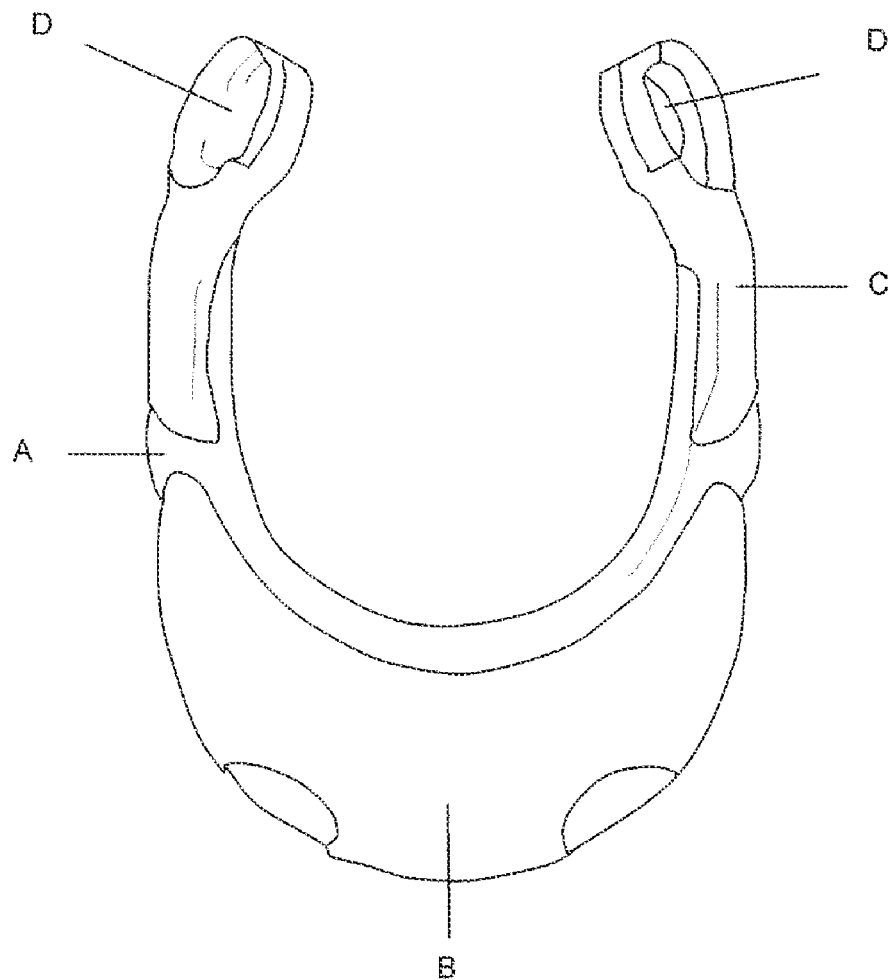
FIG. 1 shows a general schema of the buccal device.
Figure 2A:
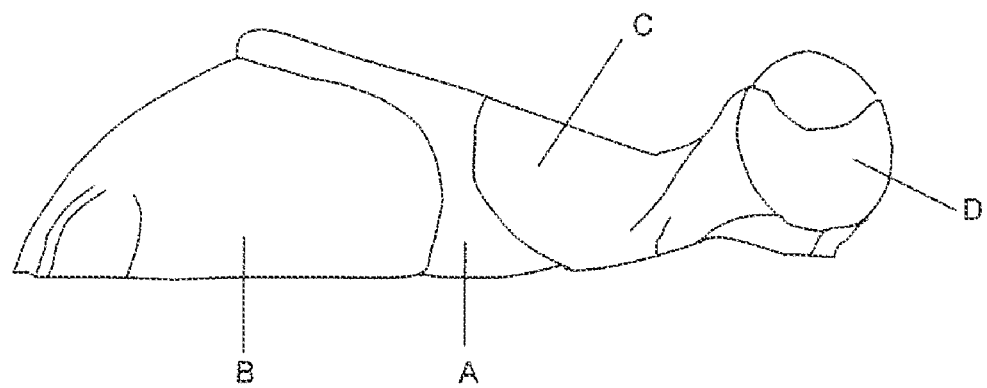
FIG. 2A is a right side view of the buccal device.
Figure 2B:
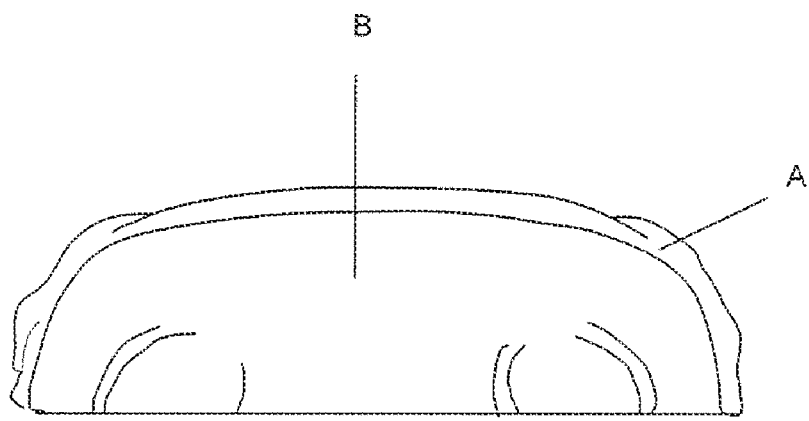
FIG. 2B is a front view of the buccal device.
Figure 2C:
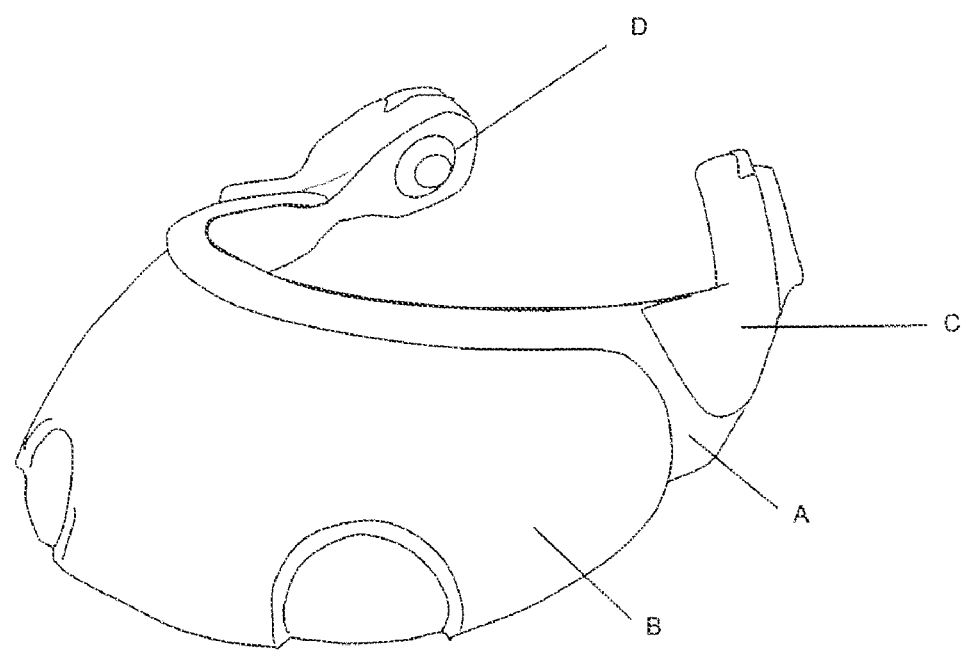
FIG. 2C is a perspective view of the buccal device.
Figure 3A:
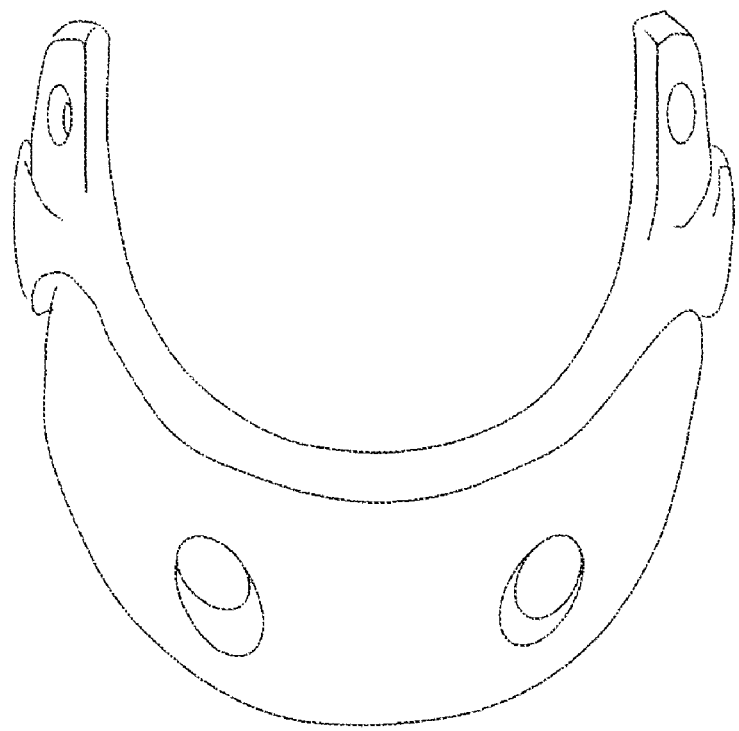
FIG. 3A is an elevated view of the fixed lower piece or main piece.
Figure 3B:
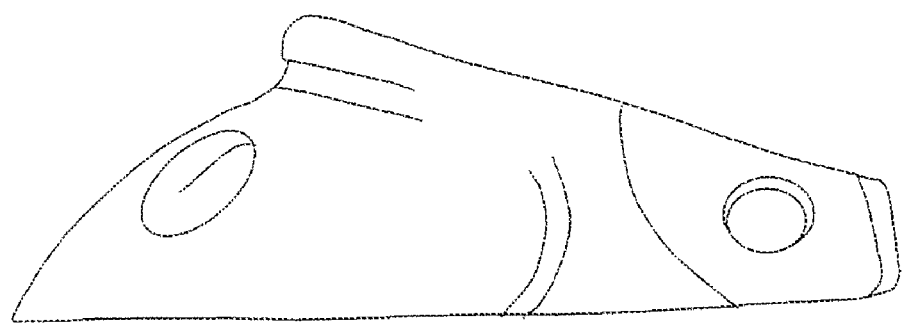
FIG. 3B is right side view of the fixed lower piece or main piece.
Figure 3C:
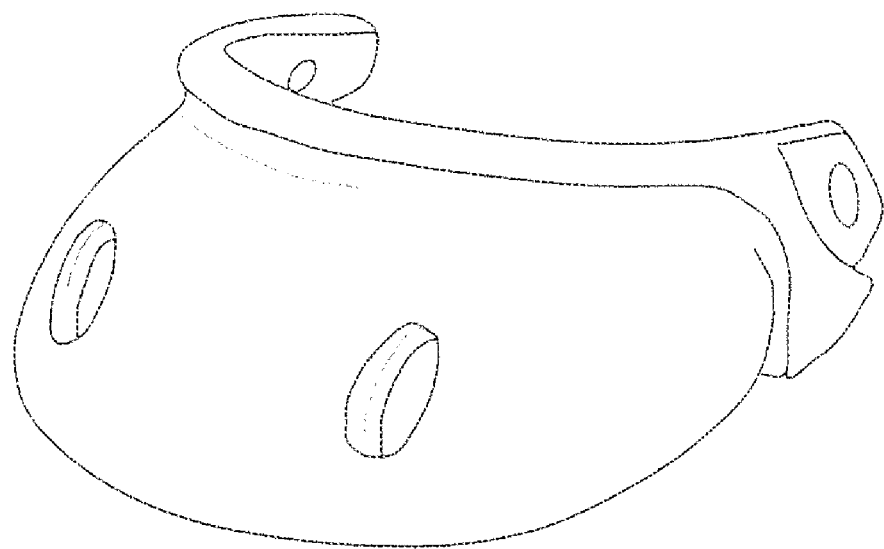
FIG. 3C is a perspective view of the fixed lower piece or main piece.
Figure 4A:
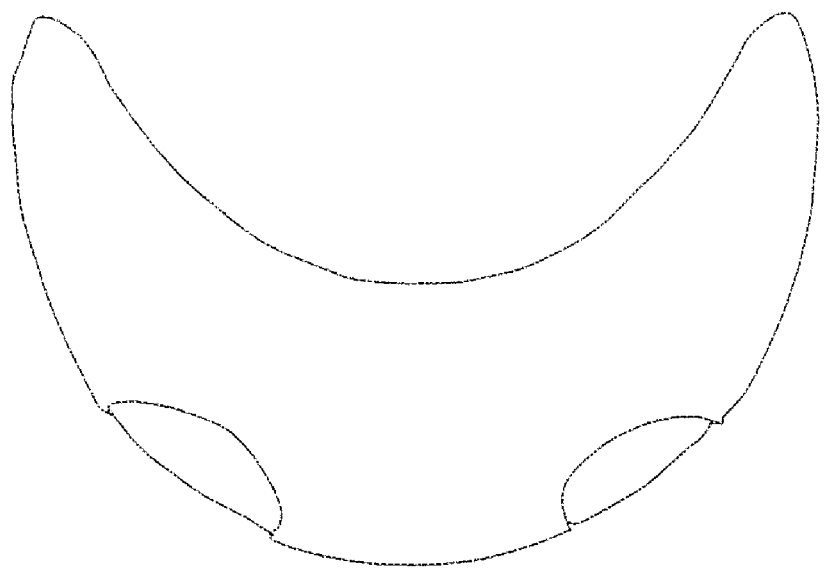
FIG. 4A is an elevated view of the lower cover.
Figure 4B:
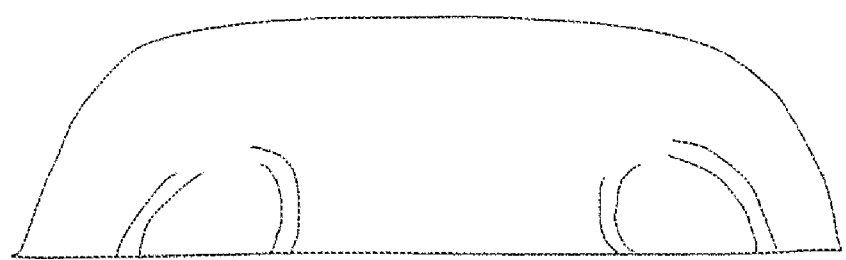
FIG. 4B is a front view of the lower cover.
Figure 4C:
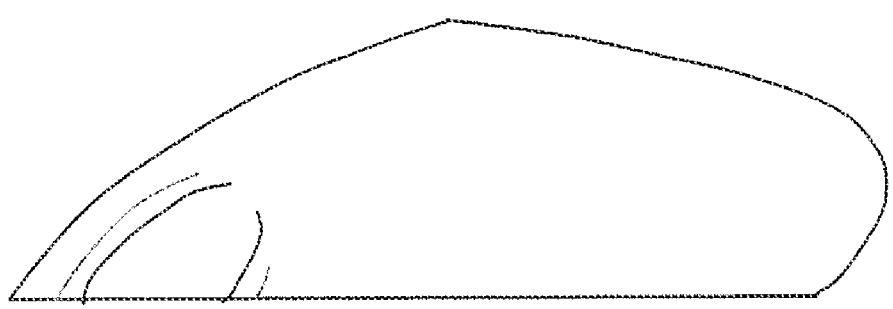
FIG. 4C is a right side view of the lower cover.
Figure 4D:
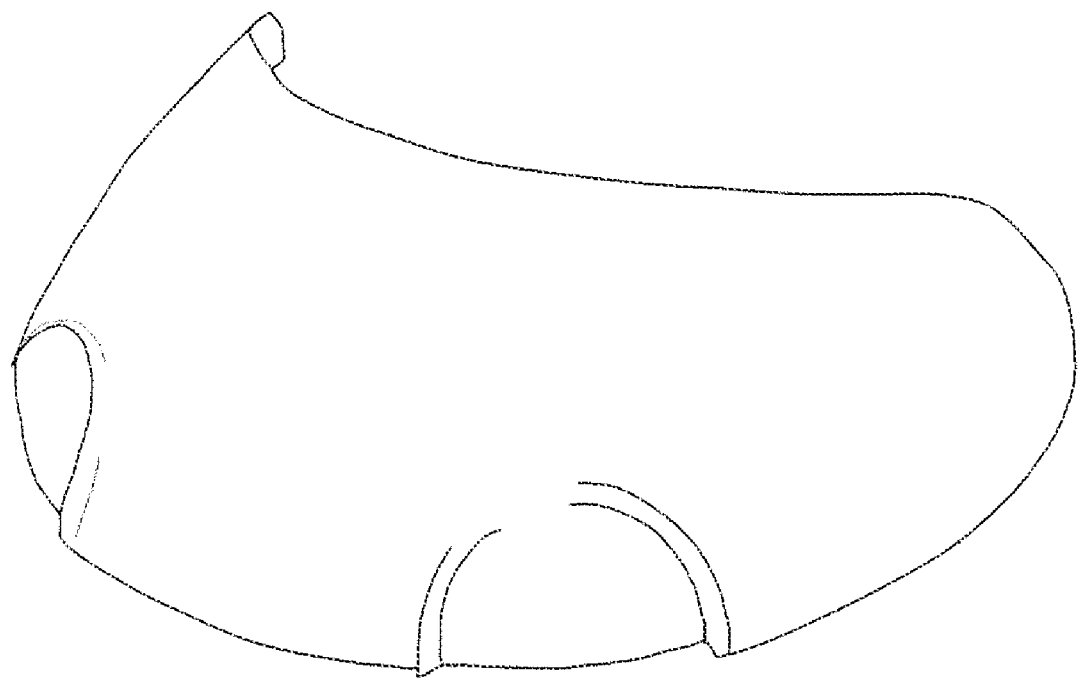
FIG. 4D is a perspective view of the lower cover.
Figure 5A:
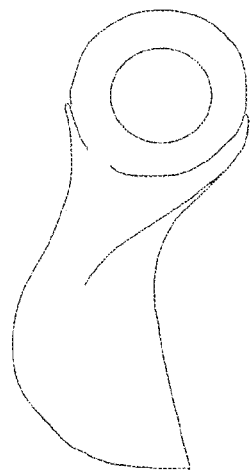
FIG. 5A is a front view of the left side removable piece.
Figure 5B:
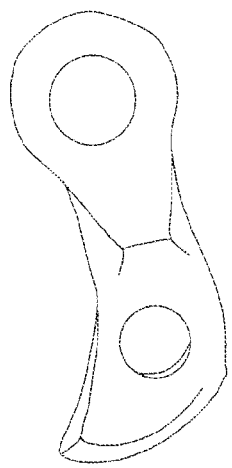
FIG. 5B is a back view of the left side removable piece.
Figure 5C:
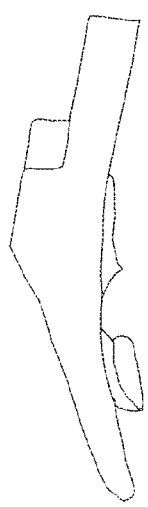
FIG. 5C is a side view of the left side removable piece.
Figure 5D:
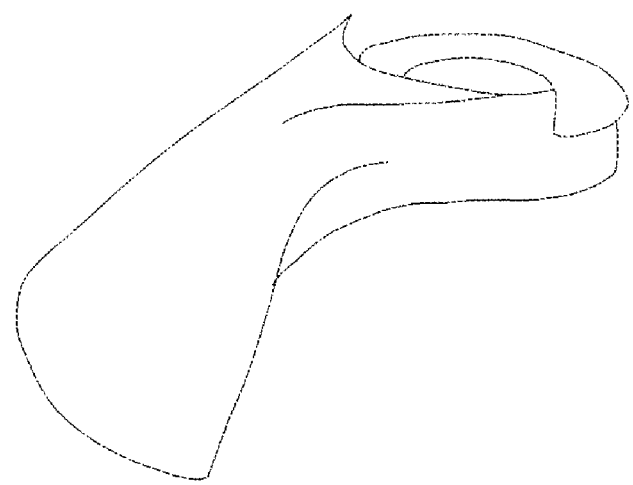
FIG. 5D is a perspective view of the left side removable piece, front face.
Figure 5E:
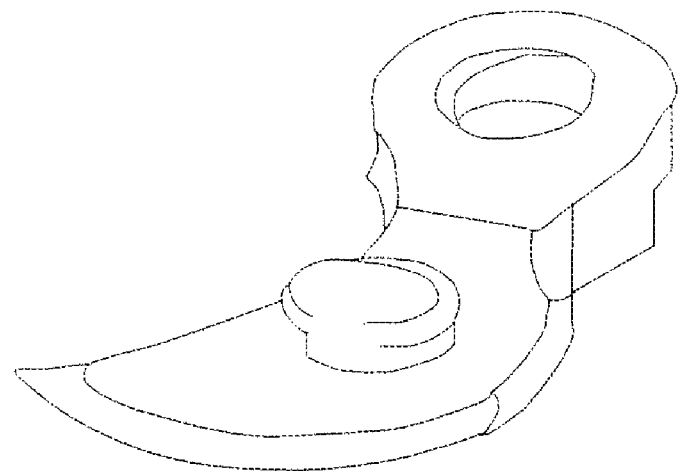
FIG. 5E is a perspective view of the left side removable piece, back face.
Figure 6A:
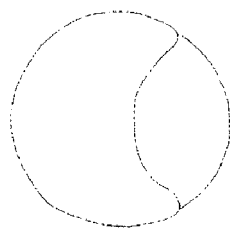
FIG. 6A is an elevated view of the upper circular cover.
Figure 6B:
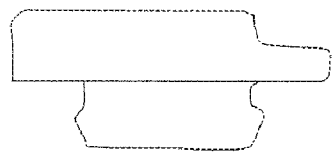
FIG. 6B is a side view of the upper circular cover.
Figure 6C:
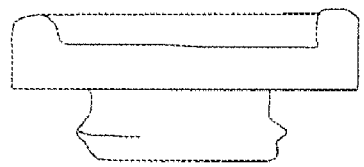
FIG. 6C is a front view of the upper circular cover.
Figure 6D:
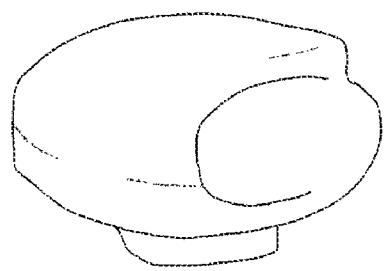
FIG. 6D is a perspective view of the upper circular cover.

The fixed lower piece or main piece (A) is the body of the device to which the other parts are attached. It has circular perforations in front to attach the lower cover (B), and in the sides of the upper ends to attach the removable pieces (C). It has a U shape with rounded edges in the lower area and is concave towards the center, as can be seen in FIGS. 3A to 3C.

The lower cover (B) has a similar design to the main piece, because the two pieces are attached to each other. It has two interior perforations that serve to attach it to the main piece using a pressing action, allowing the installation and maximum stability of the rubber dam between these pieces (see FIGS. 4A to 4D). It is concave towards the center with a U shape, the upper ends of which are rounded.

The two removable pieces (C) have the same form as each other, only varying in that one is left and the other is right. They have a special characteristic in that they can be moved to the side to facilitate the taking of x-rays under the device and the rubber dam, without being removed during the isolation of the tooth, which also facilitates the use of the ejector. The upper covers (D) are placed on these pieces (C), so that they are provided with circular protuberances on the upper ends, used to attach the rubber dam, and their lower part has a circular protuberance that is attached to the main piece, as can be seen in FIGS. 5A to 5E. It is circular at the upper end, with a narrower section in the center, connected to a lower end, of which the external side is rounded and the internal side is pointed.

The lower section of the upper circular covers (D) has a smooth neck with an end part that is wider with a bigger diameter, allowing attachment to the removable pieces by pressing. The upper section of the cover has a cavity, facilitating the use of these pieces, as can be seen in FIGS. 6A to 6D.

All the pieces are self-attaching and are made of a silicone rubber material. This material was chosen principally for its low toxicity, resistance to high temperatures, malleability and because it can be inserted easily into other pieces of the same material. In addition, it offers high durability and produces an attractive product.

The pieces of the device are attached to each other by simply using pressure. One piece, called the male, is inserted into another, called the female, helped by the type of material of the pieces, which can easily be assembled and pulled apart.

This invention device, in addition to isolating the teeth to be treated, can be adapted to the patient's face and facilitates the attachment of the rubber dam, as well as including a part that can be moved to the side in order to place an ejector through the lower section at the moment of operation, making it possible to take x-rays without the need to remove the device.

The device is suitable for all types of patients and can be produced in different sizes according to age, that is, approximately 0.03-0.09 m long and 0.05-0.12 m wide, with an approximate weight below 60 g. Each piece of the device has a distinctive color, which facilitates rapid assemblage, but, more importantly, contributes to acceptance by children, which does not normally occur at the present time with dental tools. Therefore yellow has been chosen for the pieces that are constantly being moved, that is to say, the covers, both upper (D) and lower (B). Violet is a neutral color, which in this case indicates attachment and/or movement, so it is used for the removable upper pieces (C), which can be moved aside to take x-rays or to quickly and easily use the ejector Finally, the stable color blue is used for the fixed lower piece or main piece (A), to which the remaining parts of this device are attached.

The method of use of the buccal device in the patient's mouth comprises the following steps:
 installing the rubber in the device, between the main piece and the removable pieces (C);
 placing the lower cover (B) to attach the rubber completely;
 assembling the upper covers (D);
 attaching the covers and verifying that they are tight and that the rubber will not come off;
 perforating the rubber with a suitable instrument;
 placing the corresponding clamp;
 positioning the device on the patient's face;
 positioning the ejector under the device;
 isolating the tooth; and
 initiating the clinical work inside the patient's mouth.

EXAMPLE OF AN APPLICATION

Manufacture of the Pieces of the Device

Figure 7:
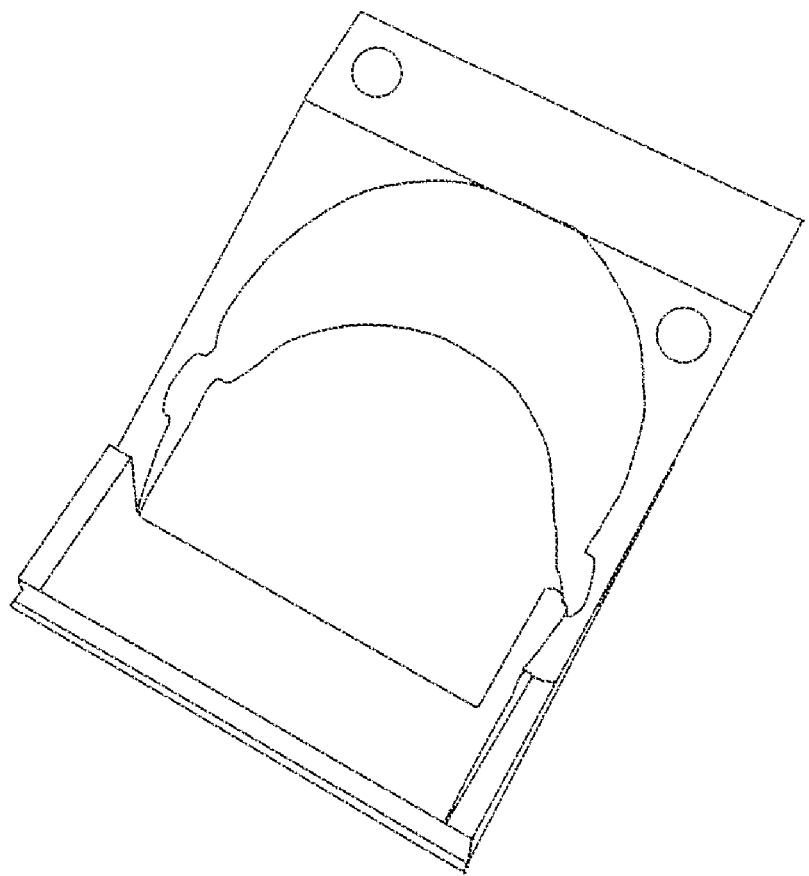
FIG. 7 is the mold for the production of the main piece.

To manufacture the different pieces that form the device, first matrixes were made using a tri-dimensional modeling program, which allowed the 3D drawing to be exported to the real solution through mechanization of the pieces by CNC numerical control, which produced the matrixes with precision cutting. These matrixes were made of steel, and in most cases two matrixes were used for each piece. Then a conventional silicone injection process was used, with the flow directed into a molding system for all the pieces that constitute the buccal device. FIG. 7 schematizes the mold produced for the manufacture of the main piece.

The device obtained was of different sizes depending on the age of the patient: thus a device 0.04 m high and 0.06 m wide was used for children aged from 3 to 5 years old; a device 0.06 m high and 0.08 m wide was used for ages 6 to 8; and a device 0.08 m high and 0.1 m wide for ages 9 to 11.

This device was tested by three dentists and 4 patients of the ages previously mentioned. They found it easy to use, an excellent device for absolute isolation of the working area, and visually attractive.

The invention claimed is:

1. A dental device for isolating a working area, comprising:
 a substantially concave main piece having two upper ends and a substantially round edge on a lower area of the main piece, the round edge being adaptable to a patient's mouth;
 a substantially concave lower cover attached to the lower area of the main piece;
 two removable pieces each attached to each of the two upper ends of the main piece;
 two upper covers each attached to each of the two removable pieces, the upper covers each having a protuberance to allow attachment of a rubber dam.

2. The dental device of claim 1, wherein the lower area of the main piece has one or more perforations to allow attachment of the lower cover, and the upper ends of the main piece each has a perforation to allow attachment of each of the two removable pieces.

3. The dental device of claim 1, wherein the lower cover has one or more notch for attaching to the main piece.

4. The dental device of claim 1, wherein the removable pieces each has a circular upper end, a narrower center section and a lower end, the lower end having a round external side and a pointed internal side.

5. The dental device of claim 1, wherein the removable pieces are movable to allow passing of x-rays.

6. The dental device of claim 1, wherein the protuberance of the upper covers each has a smooth neck, a widened end, and/or a cavity on an upper part of the upper cover to allow attachment of the upper covers to the removable pieces.

7. The dental device of claim 1, wherein the main piece, the lower cover, the removable pieces and the upper covers are made of silicone rubber.

8. The dental device of claim 1, wherein the dental device has a length of from about 0.03 meters to about 0.09 meters, a width of from about 0.05 meters to about 0.12 meters, and a weight of about 60 grams.

9. A method for providing isolation of a working area in a patient's mouth, comprising:
 1) placing a rubber dam on top of a substantially concave main piece having two upper ends and a substantially round edge in a lower area of the main piece, the round edge being adaptable to a patient's mouth, each of the two upper ends being attached to a removable piece;
 2) attaching a substantially concave lower cover to the lower area of the main piece so that the rubber dam is secured between the lower area of the main piece and the lower cover;
 3) attaching an upper cover to each of the removable pieces, the upper covers each having a protuberance to allow attachment of a rubber dam;
 4) attaching the rubber dam to the upper covers;
 5) making a perforation on the rubber dam at a suitable position with a suitable size for isolation of a tooth;
 6) positioning the main piece and the rubber dam on the patient's face; and
 7) isolating the tooth through the perforation of the rubber dam, thereby providing isolation of a working area in the patient's mouth.

* * * * *